United States Patent

Forst et al.

[11] Patent Number: 6,071,291
[45] Date of Patent: Jun. 6, 2000

[54] MICRO DYNAMIC MESH

[75] Inventors: Peter Forst, Emmendingen; Erhard Reisberg, Mengen, both of Germany

[73] Assignee: Howmedica Leibinger GmbH & Co. KG (Leibinger), Germany

[21] Appl. No.: 09/176,293

[22] Filed: Oct. 21, 1998

[30] Foreign Application Priority Data

Oct. 21, 1997 [DE] Germany .......................... 197 46 396

[51] Int. Cl.$^7$ ................................................. A61B 17/08
[52] U.S. Cl. ............................................................ 606/151
[58] Field of Search ....................................... 606/151, 69

[56] References Cited

U.S. PATENT DOCUMENTS

| | | |
|---|---|---|
| 5,346,492 | 9/1994 | Morgan ...................................... 606/60 |
| 5,468,242 | 11/1995 | Reisberg . |
| 5,509,933 | 4/1996 | Davidson et al. ......................... 623/16 |
| 5,743,913 | 4/1998 | Wellisz ...................................... 606/69 |
| 5,752,958 | 5/1998 | Wellisz ...................................... 606/69 |

*Primary Examiner*—Michael Buiz
*Assistant Examiner*—Vy Q. Bui
*Attorney, Agent, or Firm*—Lerner, David, Littenberg, Krumholz & Mentlik, LLP

[57] ABSTRACT

A lattice for the fixation of bone parts or for the bridging of bone defects, particularly in the region of the skull and jaw, is made of biocompatible material with a reticular structure and with recesses for receiving bone screws, with which the lattice can be secured on the bone. The lattice does not have circular rings for receiving bone screws, but instead each lattice recess (32) can be used for receiving a bone screw. The bridges form meandering, continuous, regular bridge rows along the main axes of the lattice.

32 Claims, 2 Drawing Sheets

MICRO DYNAMIC MESH

The invention relates to a lattice for the fixation of bone parts or for the bridging of bone defects, particularly in the region of the skull and jaw, and made of biocompatible material with a reticular structure.

Such a lattice is known from U.S. Pat. No. 5,468,242. Formable lattice implants of this type are used for the fixation and immobilization of bone fragments at one or more bone fracture sites and in particular also as a three-dimensionally formable material which is secured on the bone by means of bone screws. Lattices such as these can cover not only flat areas of bone, but also curved bone surfaces, including concave, convex or spherical surfaces, in which cases different areas of the lattice have to be stretched to different extents, while other areas of the lattice do not have to be stretched or, in rare cases, even have to be compressed. In the cited prior art document, circular rings, which are distributed uniformly in the mesh, are used for receiving the bone screws. These rings to a certain extent restrict the stretchability and formability of the lattice. In said prior art document, there are bridges extending between the receivers for the bone screws. These bridges of the lattice do not form points of intersection, but instead the bridges (termed arms in said prior art document) lie between the circular receivers for the bone screws, which in each case lie at the mesh intersections of the lattice. These lattices are used mainly for bridging defects in non-load-bearing bone areas.

The invention is based on the object of further developing the three-dimensionally formable lattice (specialist term "mesh") mentioned above in such a way as to obtain a still further improved three-dimensional flexibility. In doing so, however, the aim is to ensure that, even upon maximum utilization by widening and/or stretching of the lattice, the perforations of the lattice should also remain small enough to prevent soft tissue parts from growing through and thus penetrating into cavities, while on the other hand, however, the exchange of fluid through the lattice should not be obstructed.

According to the invention, this aim is achieved by the fact that the lattice of the abovementioned type has a multiplicity of lattice points at which curved lattice bridges end.

A lattice point is here to be understood as a point (a site) of the flat lattice at which several, but at least three, bridges of the lattice end. In other words, at least three bridges converge at the lattice point. The expression "point" is not to be understood here in mathematical terms, but in technical terms, in the sense of a defined area of the lattice. In accordance with the above definition of a lattice point, a bridge is here understood as the material connection of adjacent lattice points, which material connection neither divides nor branches between its ends, but can be straight or can be bent in the lattice plane. If four bridges end at a lattice point, the latter is here also referred to as a point of intersection. Where, in the prior art, the bridges end in a ring which is used for receiving a bone screw, this is not a lattice point, since in said prior art the bridges do not end at the lattice point, i.e. do not converge at the lattice point.

A sequence of contiguous bridges which together form the shortest possible continuous line in the direction of a main axis of the lattice is here referred to as a bridge row (in the illustrative embodiments of the invention, a bridge row is not a straight line). Moreover, the expression "main axes of the lattice" refers hereinbelow to the direction of those straight lines which connect those adjacent lattice points of a given lattice point which, of all possible pairs of lattice points, are at the greatest distance from one another. This is represented in FIG. 4. Starting out from a lattice point, the bridges thus join together to form meandering lines, said meandering lines running in the direction of the main axes.

According to one aspect of the invention, a lattice for the fixation of bone parts or for the bridging of bone defects, of the abovementioned type, is proposed in which the lattice has no circular receivers for bone screws, but instead each lattice recess is designed for receiving a bone screw, and the bridge rows of the lattice form a continuous regular undulating line, said undulating line preferably having a relatively soft (round) and approximately sinusoidal structure.

A lattice of this type permits a high degree of three-dimensional flexibility together with a high degree of stability. In doing so, the sizes of the recesses in the lattice can be kept so small that tissue does not grow through the lattice during the healing process, while at the same time, however, a substantially unobstructed exchange of fluid through the tissue is made possible. As regards the positions for the bone screws, the operating surgeon has a greater number of possible choices than in the prior art cited above.

According to a preferred embodiment of the invention, hereinafter referred to as "mesh 1", all the bridges between all the lattice points of the lattice are curved in at least two opposite directions.

In the illustrative embodiment of the invention according to FIG. 1 (mesh 1), the lattice points bordering a recess of the lattice form a rectangle, in particular a square. Each lattice point is connected to each of its four adjacent lattice points via one bridge in each case.

A further particularly preferred variant of the invention, hereinafter referred to as "mesh 2", achieves the aforementioned technical objectives, in particular a still greater stretchability and tear strength compared to mesh 1, by virtue of the fact that the lattice points are arranged at the corners of a hexagonal honeycomb pattern and are connected via bridges which are curved in only one direction, preferably designed as semicircles. In this variant of the invention, the six bridges bordering a recess are curved alternately outwards and inwards, viewed from the centre point of the recess.

Illustrative embodiments of the invention are explained in greater detail hereinbelow with reference to the drawing, in which:

FIGS. 1 and 3 show lattices for the fixation of bone parts or for the bridging of bone defects, in particular for the reconstruction of defects of the cranium, the eye sockets and the walls of the paranasal sinuses, and also for reconstruction in the jaw area and also for augmentation of the alveolar ridge.

Figure 1:
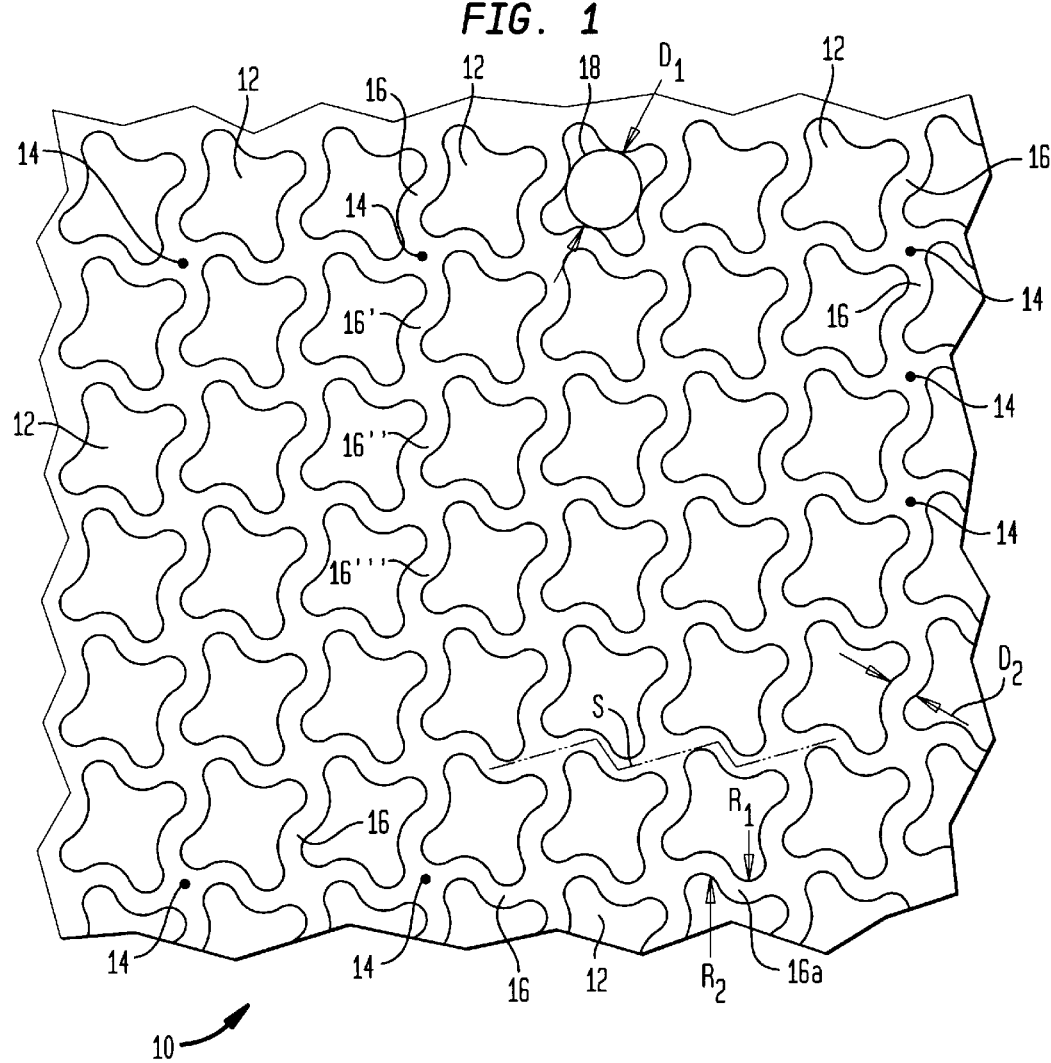
FIG. 1 shows a lattice according to the invention on a greatly enlarged scale.
Figure 3:
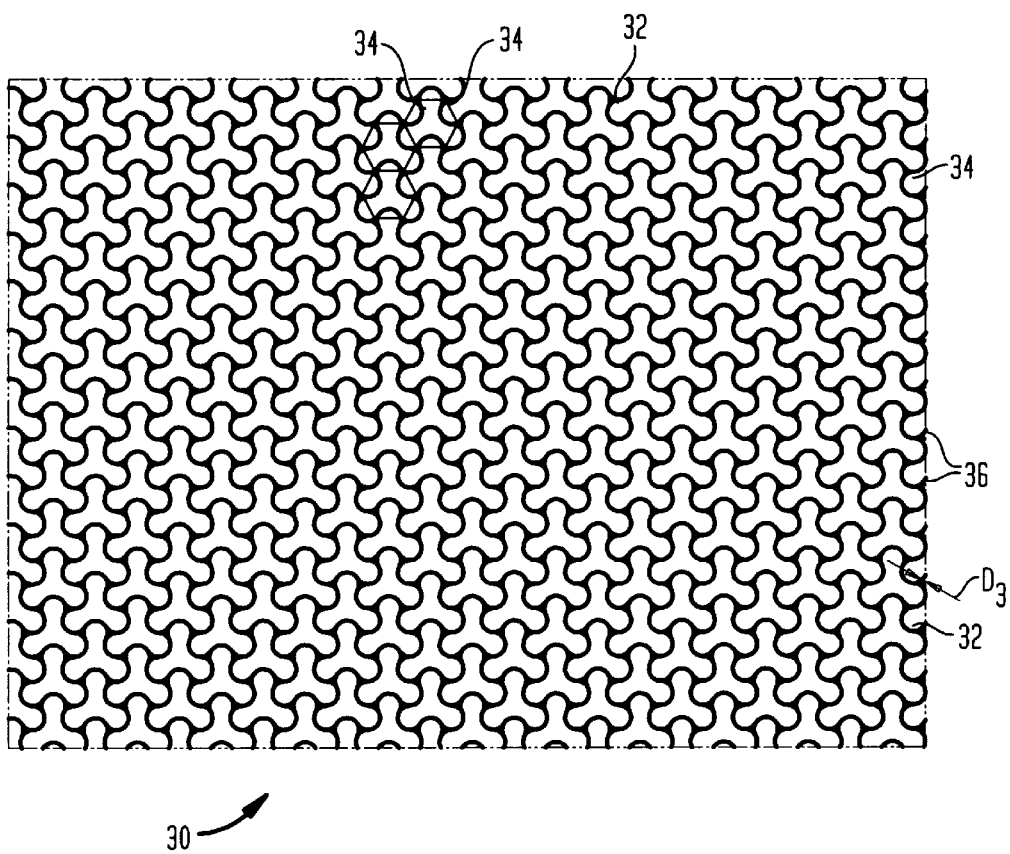
FIG. 3 shows a further illustrative embodiment of a preferred lattice according to the invention, on a greatly enlarged scale.

The thickness of the lattice 10 or 30 perpendicular to the plane of the drawing according to FIGS. 1 and 3 is less than 0.5 mm, more preferably less than 0.3 mm, particularly preferably less than 0.2 mm and very particularly preferably less than 0.15 mm.

The width $D_2$ or $D_3$ of each bridge between the lattice points 14 or 34 is preferably less than 2 times the thickness, and more preferably less than 1.5 times the thickness, of the lattice perpendicular to the plane of the drawing.

Lattices with the abovementioned dimensions and with the structures shown in FIGS. 1 and 3 can preferably be etched from titanium.

In FIG. 1, the lattice 10 is enlarged by about 16 times compared to its actual dimensions and only a section is shown, i.e. the right and lower edges of the lattice have been cut away, for example with suitable scissors.

Figure 2:
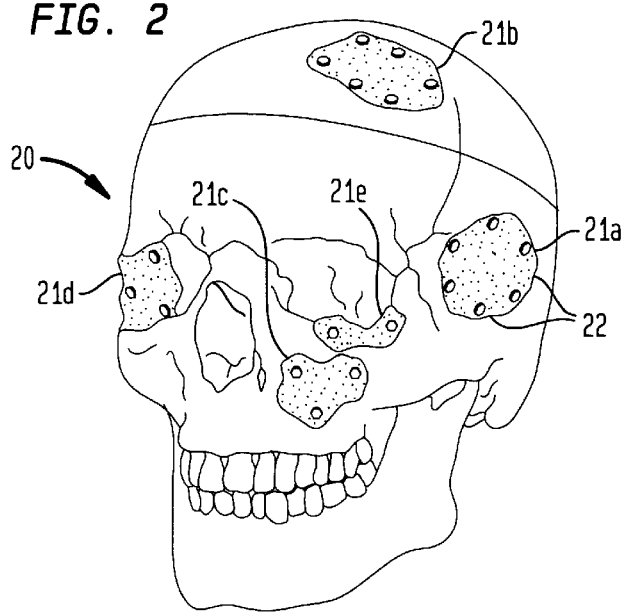
FIG. 2 shows examples of applications of a lattice according to FIG. 1 or 3 on the human skull or jaw.

In FIG. 2, lattices 10 and 30 are shown diagrammatically in different applications on a human skull, in the form of lattices 21a, 21b, 21c, 21d and 21e which have been cut to different sizes and which are bent three-dimensionally for the fixation of different bone parts and for the bridging of bone defects and are secured on the bone by means of bone screws 22. To this extent, the use of the lattices according to the invention corresponds to the prior art discussed at the outset.

According to FIG. 1, the lattice 10 has a multiplicity of uniformly shaped recesses 12 into which bone screws 22 can be inserted as desired. Bridges 16 between lattice points 14 of the reticular lattice 10 are in each case curved in an S shape (in the opposite directions $R_1$, $R_2$). This curvature permits a slight bending of the lattice according to the requirements of the bone defect. As FIG. 1 shows, the lattice 10 has no special circular receivers for the bone screws. Instead, the bone screws can be pushed through any desired recess 12, and the cloverleaf-shaped configuration of the recesses 12 as seen in FIG. 1 affords good bearing surfaces for the head of the bone screw on the lattice 10, namely on four projections, each offset by 90°, of the bridges 16 of the lattice.

As FIG. 1 also shows, bridges 16, 16', 16" 16''', etc., merging with one another in one direction, form a continuous regular undulating line having an approximately rounded sawtooth structure. This sawtooth structure is indicated in FIG. 1 by a broken line S.

A circle 18 can be described in a recess 12, the diameter D1 of this circle 18 being preferably smaller than 2 mm, more preferably smaller than 1 mm, and particularly preferably smaller than 0.8 mm. The circle touches each of the curves of the bridges 16 protruding into the recess 12. Correspondingly, a screw head (not shown) which is slightly larger in diameter than the circle 18 overlaps the bridges 16 at these curvature points, and does so at regular intervals of in each case 90° about its circumference, so that a uniform contact pressure and gripping by the screw head is ensured.

FIG. 3 shows a further embodiment of a lattice which is improved compared to the above-described lattice, in particular in respect of tear strength and stretchability. Otherwise, the lattice according to FIG. 3 also has better properties in respect of the remaining technical and medical objectives mentioned in the introduction to the description.

Figure 4:
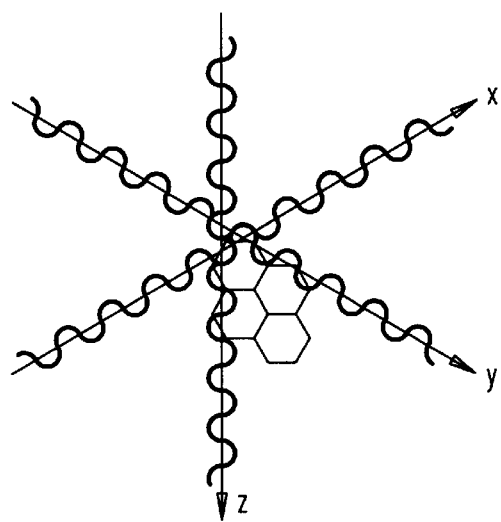
FIG. 4 shows the definition of the main lattice axes in the case of a lattice according to FIG. 3.

A lattice 30 according to FIG. 3 can be described as a structure with meandering, continuous, regular bridge rows along the main axes x, y, z of the lattice (cf. the above definition), in each case starting from a lattice point. FIG. 4 shows the definition of the main axes x, y, z of the lattice.

The circular arc curves of the bridges form in each case recesses (perforations) 32 in the lattice, the recesses 32 each being suitable for receiving a (single) bone screw. The recesses 32 are not surrounded by a complete bridge ring, and instead the bridges form only an incomplete ring, i.e. a ring which is larger than a semicircular ring, but smaller than a ring closed about 360°. As can be seen immediately from FIG. 3, the structure shown there has the special advantage that the surgeon has a very wide range of options in terms of choosing the positioning of the bone screws, i.e. bone screws can be applied at practically any location on the lattice. The receivers 32 for the bone screws are in this case essentially of the same value.

The structure of a lattice shown in FIG. 3 can also be described by means of the lattice points 34. As can be seen from FIG. 3, three bridges issue from each lattice point 34. If adjacent lattice points are connected, then regular hexagons are formed. Three hexagons are shown by way of example at the top right of FIG. 3 (the hexagon lines are only an illustrated addition to the lattice, and are not present in the actual lattice itself). The regular hexagons formed by the (imagined or illustrated) connection lines of the lattice points 34 form a honeycomb structure. Bridges running between the lattice points 34 are each designed in a semi-circular shape and curve alternately outwards and inwards.

In the illustrative embodiment according to FIG. 3, the entire lattice structure is distinguished by smoothly curved bridges, i.e. the bridges in this illustrative embodiment have no sharp kinks. The lattice shown in FIG. 3 is greatly enlarged compared to the actual lattice, approximately at a scale of 1:10.

The edge length of the hexagon, that is to say the length of a connection line of the lattice points, is for example 4 to 8 times the sheet thickness of the lattice. The sheet thickness of the lattice is the thickness of the lattice perpendicular to the plane of the drawing. In particular, the edge length of the hexagon can be 4 to 6 times the sheet thickness, preferably 4 to 5 times the sheet thickness.

The bridge width in the plane of the drawing is preferably 1 to 4 times, particularly preferably 1 to 2 times, the sheet thickness of the lattice.

The receivers 32 for the bone screws are distributed very densely over the entire lattice. The surgeon can apply the bone screws as and where required. The internal diameter of the receivers 32, which are formed by incompletely closed rings, can be defined by the maximum diameter of balls which fall straight through the receivers 32. In this sense, the internal diameter of the receivers 32 is not-more than 1 mm, in particular not more than 0.8 mm, particularly preferably not more than 0.4 or 0.6 mm.

Preferred sheet thicknesses are cited in the dependent claims.

The lattice described with reference to FIG. 3 permits extreme stretching, and even in the greatly deformed state the sizes of the perforations (recesses 32) remain largely unaffected. The described structure permits substantial adaptation of the stiffness of the lattice, depending on the choice of sheet thickness and bridge width.

What is claimed is:

1. Lattice for the fixation of bone parts or for the bridging of bone defects, particularly in the region of the skull and jaw, and made of biocompatible material, wherein the lattice has a multiplicity of lattice points at which a plurality of curved lattice bridges end, said lattice bridging surrounding a recess having at least three concave portions where in all bridges between all the lattice points are curved in at least two opposition directions and wherein the lattice recesses are used for receiving bone screws.

2. Lattice according to claim 1, wherein said lattice has no circular receivers for bone screws.

3. Lattice according to claim 1 wherein the bridges between two lattice points are curved in an S shape.

4. Lattice according to claim 3 wherein the bridges between two lattice points are curved in a zigzag shape.

5. Lattice according to claim 1 wherein a circle laid in the recesses of the lattice and just about touching the bridges has a diameter smaller than 2 mm,.

6. Lattice according to claim 5 wherein the average size of a recess of the lattice lies in the region of 90% to 150% of the thickness of the lattice material in the direction perpendicular to the lattice plane.

7. Lattice according to claim 1 wherein adjoining bridges of the lattice form a continuous undulating line.

8. A lattice for the fixation of bone parts or for the bridging of bone defects, particularly in the region of the skull and jaw, and made of biocompatible material, comprising a multiplicity of lattice points at which curved continuous lattice bridges end, said continuous lattice bridges forming a recess for receiving bone screw, wherein the lattice points bordering a recess form a regular hexagon wherein the bridges between the corner points of the hexagon are curved alternatively outwardly and inwardly, viewed from the center point of the recess in particular in a semicircular shape.

9. Lattice according to claim 8 wherein the lattice has no closed circular rings for receiving bone screws.

10. Lattice according to claim 8 wherein the bridges form not completely closed rings for receiving bone screws.

11. Lattice according to claim 10 wherein the internal diameter of incompletely closed rings for receiving bone screws is smaller than 1 mm.

12. Lattice according to claim 8 wherein there are meandering, continuously round bridge rows.

13. Lattice according to claim 8 wherein there are meandering bridge rows consisting of semicircular sections.

14. Lattice according to claim 8, wherein the edge length of the hexagon is 4 to 8 times the sheet thickness of the lattice.

15. Lattice according to claim 8 wherein the bridge width at all lattice sites is essentially uniform.

16. Lattice according to claim 15 wherein the bridge width is 0.8 to 4 times the sheet thickness of the lattice.

17. Lattice according to claim 8 wherein said lattice is made of titanium.

18. Lattice according to claim 17 wherein said lattice is etched.

19. Lattice according to claim 14 wherein the thickness of the lattice material in the direction perpendicular to the lattice plane is smaller than 0.5 mm.

20. Lattice according to claim 19 wherein adjoining bridges of the lattice which run essentially in the same directions, are formed as a continuous undulating line.

21. The lattice according to claim 8, wherein the edge length of the hexagon is 4 to 8 times the sheet thickness of the lattice.

22. A bone defect bridging lattice plate for use with bone screws having a threaded screw shank and a screw head including a bearing portion, the lattice plate comprising a plurality of lattice points connected by lattice bridges, the lattice bridges spaced to define a recess for receiving said screw shank and oriented such that less than the entire bearing portion of each screw head is supported by the lattice bridges adjacent said recess wherein said lattice bridge is curved and has a projecting portion with the screw head bearing on the projection portion of at least three lattice bridges forming said recess.

23. The lattice plate as set forth in claim 22, wherein the screw head bears on projections on four lattice bridges.

24. The lattice plate as set forth in claim 22, wherein the bearing portion of the screw head extends circumferentially for 360° and the bearing portion supported by the lattice bridges is greater than 180° but less than 360°.

25. The lattice plate as set forth in claim 22, wherein the curved lattice bridges follow a continuous undulating line.

26. The lattice plate as set forth in claim 22, wherein a circle laid in the recess for receiving the screw shank formed by the lattice bridges has a diameter less than 2 mm.

27. The lattice plate according to claim 22, wherein the average size of a recess of the lattice plate lies in the region of 90% to 150% of the thickness of the lattice material in the direction perpendicular to the lattice plane.

28. The lattice according to claim 22, wherein the bridge width is 0.8 to 4 times the sheet thickness of the lattice.

29. The lattice according to claim 22, wherein the lattice plate has a thickness in the direction perpendicular to the lattice plane smaller than 0.5 mm.

30. The lattice plate as set forth in claim 22, wherein said lattice bridges surrounding each recess have at least three concave portions.

31. The lattice according to claim 22, wherein adjoining bridges of the lattice, are formed as a continuous undulating line.

32. The lattice plate as set forth in claim 22, wherein the curved lattice bridges form at least part of the periphery of the lattice plate.

* * * * *

UNITED STATES PATENT AND TRADEMARK OFFICE
CERTIFICATE OF CORRECTION

PATENT NO. : 6,071,291
DATED : June 6, 2000
INVENTOR(S) : Forst, et. al.

It is certified that error appears in the above-indentified patent and that said Letters Patent is hereby corrected as shown below:

Col. 4, line 55, "where in" should read --wherein--.

Col. 5, line 14, "comer" should read --corner--.

Col. 5, line 16, after "recess" insert --,--.

Col. 5, line 37, "17" should read --8--.

Col. 5, line 39, "14" should read --1--.

Signed and Sealed this

Tenth Day of April, 2001

*Attest:*

NICHOLAS P. GODICI

*Attesting Officer*     *Acting Director of the United States Patent and Trademark Office*